United States Patent

Lawes et al.

[11] Patent Number: 5,879,402
[45] Date of Patent: Mar. 9, 1999

[54] METHOD AND APPARATUS FOR IMPLANTING AN ACETABULAR CUP

[75] Inventors: Peter Lawes, Maidenhead; Robin S. M. Ling, South Devon, both of England

[73] Assignee: Howmedica International Inc., Shannon, Ireland

[21] Appl. No.: 651,403

[22] Filed: May 22, 1996

Related U.S. Application Data

[63] Continuation of Ser. No. 329,353, Oct. 26, 1994, abandoned.

[30] Foreign Application Priority Data

Oct. 29, 1993 [GB] United Kingdom .................. 9322383

[51] Int. Cl.$^6$ ........................................... A61F 2/34
[52] U.S. Cl. .................................. 623/22; 606/9
[58] Field of Search ................... 623/16, 18, 22, 623/23; 606/91, 92, 93, 94

[56] References Cited

U.S. PATENT DOCUMENTS

| | | | |
|---|---|---|---|
| 4,711,233 | 12/1987 | Brown | 606/91 |
| 4,865,609 | 9/1989 | Roche | 623/23 |
| 5,098,437 | 3/1992 | Kashuba et al. | 606/89 |
| 5,133,765 | 7/1992 | Cuilleron | 623/22 |
| 5,181,918 | 1/1993 | Brandhorst et al. | 606/92 |
| 5,201,779 | 4/1993 | Shiao | 623/8 |

FOREIGN PATENT DOCUMENTS

| | | |
|---|---|---|
| 0073604A1 | 3/1983 | European Pat. Off. . |
| WO 8504567 | 10/1985 | WIPO . |

*Primary Examiner*—David Isabella
*Attorney, Agent, or Firm*—Peter C. Richardson; Lawrence C. Akers; Raymond W. Augustin

[57] ABSTRACT

A method of implanting an acetabular cup which includes the step of preparing an acetabular socket to receive a cup, placing cement in the acetabular socket before or after locating a tube in line with the acetabular socket and inserting the acetabular cup through the tube and into the socket.

20 Claims, 9 Drawing Sheets

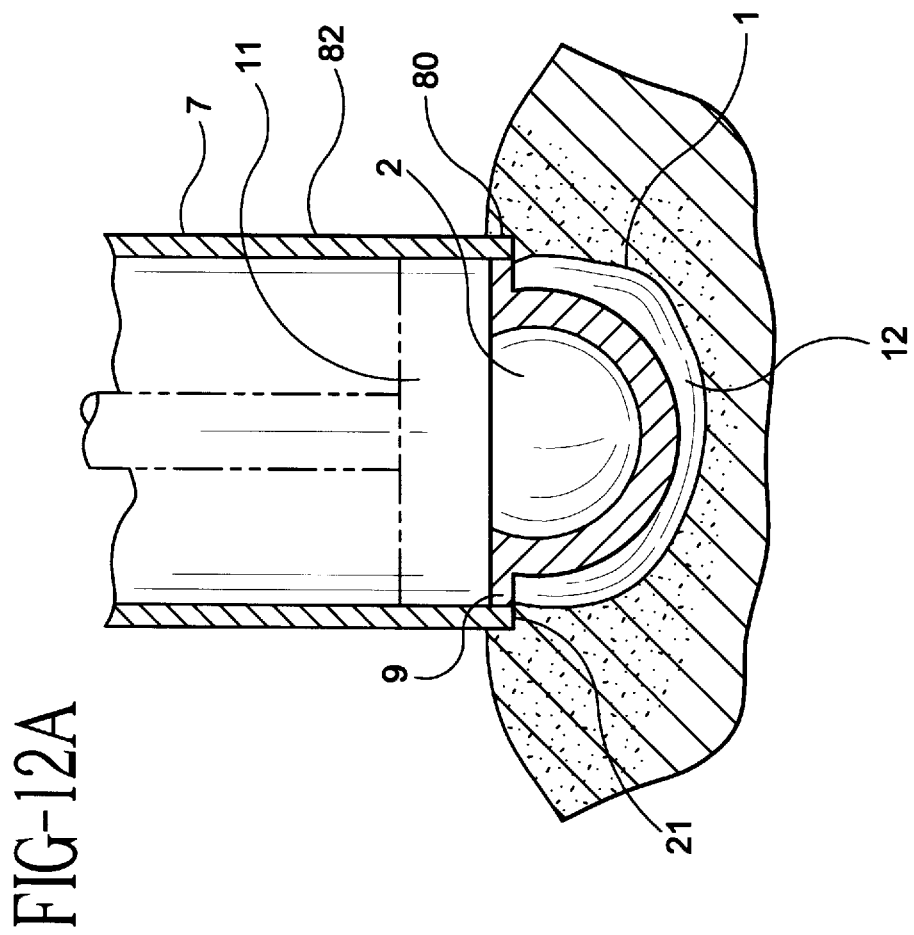

METHOD AND APPARATUS FOR IMPLANTING AN ACETABULAR CUP

This is a continuation of application Ser. No. 08/329,353, filed on Oct. 26, 1994 now abandoned.

BACKGROUND OF THE INVENTION

1. Field of the Invention

This invention relates to a method and instrumentation for implanting an acetabular cup which is to be held in place by polymethyl-methacrylate (PMMA) bone cement.

2. Description of the Prior Art

It is known, for example, to provide a flexible flange around the rim of an acetabular cup to pressurize the cement, but this only occurs as the cup approaches its final position in the acetabulum. The flexible flange touches the acetabular margin tending to occlude cement flow.

Another device for pressurizing cement is known as the Exeter Acetabular Pressurizer. In this arrangement a water filled seal mounted on the end of a handle is used after the acetabulum has been filled with cement, but before the cup is introduced, the seal covers the acetabulum and the surgeon pushes on the handle thereby forcing the doughy cement in the holes, ridges and trabeculae of the acetabulum. When the instrument is removed and the pressure is released, blood flow can squeeze between the cement and the bone.

It is also known to provide cup positioning instruments with long pointers (vertical, horizontal and at right angles to the patient's center line of body symmetry) to enable the surgeon to control cup orientation reasonably well provided the pelvis does not move. Linear positioning of the cup is determined by eye in a medio-lateral and anterio-posterior sense. If the natural acetabulum is well formed, an eyeball judgment can be acceptable, but many acetabulae are deformed or eroded, in which case eyeball judgment can be confused.

A further method is to use what are usually referred to as acetabular spacers. These can be lugs or PMMA spacer (see for example, U.S. Pat. Nos. 4,883,490 and 4,955,325) fixed to the outside of the acetabular cup or can be press studs pushed into the bone base of the natural acetabulum. These prevent the cup from being pushed too deeply into the acetabular socket and can control medio-lateral and anterio-posterior positioning. However, they force some degree of centralization of the cup. If the surgeon chooses to place the cup eccentrically to make use of a particular area of solid bone support, acetabular spacers may not permit such a placement.

SUMMARY OF THE INVENTION

It is an object of the present invention to provide a method and apparatus for overcoming some of the difficulties referred to above, to allow pressurization of the cement so that good holding is obtained and to provide a method of operation which will ensure accurate location of the cup in the socket.

According to the present invention a method of implanting an acetabular cup includes preparing an acetabular socket to receive the cup, placing bone cement in the socket before or after locating a loading tube in line with the socket and inserting the acetabular cup through the tube and into the socket by pushing it down the tube with an inserter to a predetermined position therein defined by a stop element acting on the inserter or attachment thereto.

Where the cup is provided with a flanged rim, the stop element can be arranged within the bore of the tube and the flange rim and the stop element can be constructed to allow the cup to pass the stop element but engage the inserter. Another method may include using a tube and an inserter having a stop element which engage an abutment on the tube located at a position spaced away from the end of the tube which is adjacent the socket. If desired, the position of the stop element can be adjusted prior to use.

The method may also include locating a flexible skirt assembly around the rim of the socket with the tube extending from the flexible skirt, and then inserting the acetabular cup through the tube and into the socket.

With these arrangements, it is possible to either fill the acetabulum with doughy cement and then reposition the skirt and tube assembly or the tube on the bone using markers to ensure that a previously chosen position and orientation are reestablished. Alternatively, the cement can be injected, for example by a cement gun, through the tube. The surgeon can then push the cup into the cement with the inserter to create a pressure and ensure that the cement fills all the openings in the socket. If the flexible skirt assembly is used it can be secured around the rim of the socket preventing the escape of cement and allowing it to be pressurized. The flexible skirt can be held in place by means of screws, pins and/or staples, or finger pressure alone.

The method also includes allowing some of the pressurized cement to escape from the socket and through a controlled orifice in the skirt. With this arrangement, the tube can be integral with the flexible skirt or it can be removably connected. Preferably, the flexible skirt is made From a synthetic plastics material and if it is to be left in place, could be polyethylene, polypropylene, polyurethane, or even a resorbable material for example, polyglycolic acid, or polylactic acid.

In order to locate the cup, the surgeon can control the release of cement through the orifice in the skirt, and he can push the cup with the inserter thereby feeling the desired level of cement pressure. If he is not able to reach the desired predetermined position when the stop elements are activated, he can release the pressure on the cement, allowing a little more cement to escape while the cup progresses further down the inside of the tube. An expandable tube can be used with a system for adjusting its diameter.

An advantage of the invention is that no spacers are required which may cause discontinuities in the cement mantle. The arrangement also enables the surgeon to accurately locate the position and attitude of the cup. An apparatus can also be included for positioning and orienting the tube or the tube and skirt on the bone into which the cup is to be implanted.

The invention also includes apparatus for use in the method set forth above which comprises a loading tube adapted for alignment with an acetabular socket, an inserter adapted to fit into the tube and stop elements which can act on the inserter or attachment thereto to limit movement of the inserter down the tube to a predetermined position therein. The stop element can be provided on part of the bore of the tube and act on an inner end of the inserter. This construction is particularly applicable when a flanged socket is used, the socket being provided with a gap in the flange.

In an alternative construction stop elements can be provided on the inserter which engage an abutment on said tube located at a position spaced away from the end of the tube which is intended to be adjacent the acetabular socket when in use. This construction can be used with sockets having a flange or a plain upper rim.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIGS. 12 and 12A are diagrammatic side views of apparatus similar to that shown in FIG. 11, but without the use of a skirt.

DESCRIPTION OF THE PREFERRED EMBODIMENT

Figure 1:
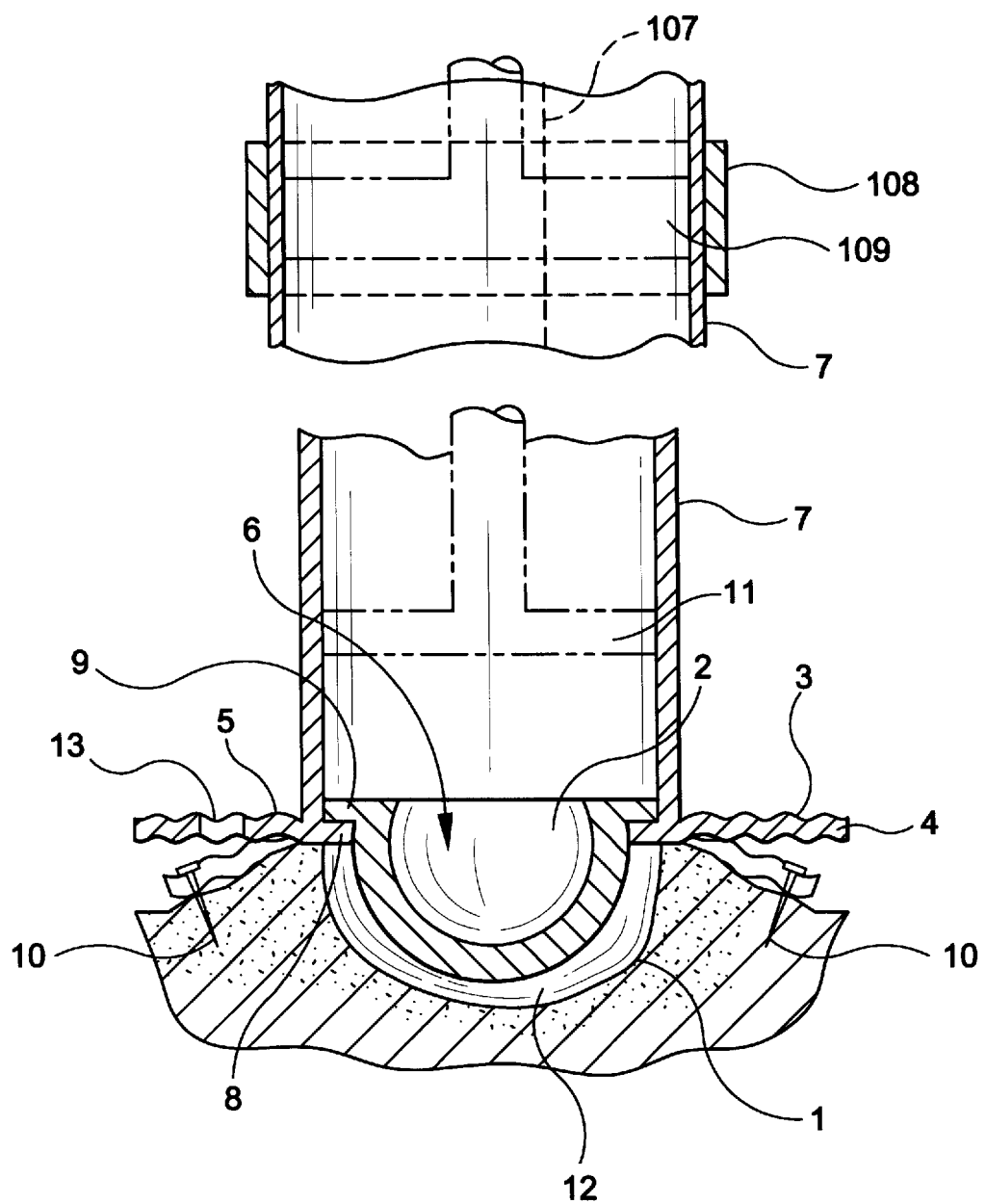
FIG. 1 is a diagrammatic cross-sectional view of one example of the apparatus showing the method of operation.

Referring to the figures, there s shown a general form of the apparatus generally denoted as 100, an acetabular socket being indicated by reference numeral 1 into which an acetabular cup 2 is to be fitted.

In order to fit the cup into the socket 1, in which it is to be held by bone cement in this embodiment, a flexible skirt assembly 3 is utilized. This skirt assembly 3 is made as an integral unit from a synthetic plastics material, for example polyethylene, polypropylene, polyurethane, or even a resorbable material, for example polyglycolic acid, or polylactic acid. The assembly comprises a flexible skirt 4 which is shown with corrugations 5. the skirt has a central opening 6 and is provided with a loading tube 7, the inner bore of which is substantially the same diameter as the opening 6. The lower end of the loading tube is formed with an inwardly projecting abutment 8. The acetabular cup 2 has an annular flange 9 having a gap 14 which is dimensioned to allow the abutment 8 to pass through it.

To implant the cup 2, the acetabular socket 1 is first prepared in the usual way for example, by reaming. The flexible skirt assembly 3 is now placed in the position shown in full lines in the drawing and the skirt 4 is bent and fixed to the bone around the acetabular opening by pins, screws or staples indicated b reference numeral 10. The deformed position of the skirt when in its secured position is indicated in broken lines. If desired, the skirt 4 can be preformed to the required shape. The relative positioning on to the acetabular bone can be controlled by positioning guides, with or without fixing.

Prior to fastening it is position, however, the position and orientation of the tube 7 are determined during the early preparatory stages of the operation and once this has been determined, the skirt 4 can be trimmed if necessary and fastened in position. It will be seen that on the right-hand side of FIG. 1 the width of the skirt 4 has been trimmed down to assist in location.

The prepared acetabulum is now filled with cement through the piston tube 7, the cement being pushed into place by a manually operated inserter in the form of a piston 11. The piston is removed when the cement is partially set and in an adequately doughy stage. The cup 2 is immediately inserted down the tube 7 using the same or an alternate inserter and thus the cement is pressurized from the moment the cup touches it. The gap 14 in the cup flange 9 is aligned with the abutment 8. In the arrangement shown, the piston 11 is used to push the cup into place the piston descending until a peripheral portion of the edge of its front face 61 engages abutment 8 thereby preventing the surgeon from pushing the cup in too far and thus locating it at a predetermined position.

As will be seen from the figures, no spacers are required in the cement mantle which now surrounds the cup and is indicated by reference numeral 12.

A cement flow release arrangement is provided by the provision of an orifice 13 in the skirt 4. The hole in the skirt is occluded, for example by the surgeon's thumb, to thus allow the pressure to build up and then allow excess cement to escape. With the cup 2 in place and the cement fully cured the tube is cut away and the remainder of the skirt left implanted. Alternatively, the tube and skirt can be removed in their entirety.

In the arrangement described above, the piston tube is integral with the skirt 4 but if desired it could be made as a separate removable item. The use of the skirt 4 also enables the position and orientation of the cup to be determined prior to actual insertion, and allows the surgeon to place it precisely where he wants it in the acetabular socket.

It will, of course, be necessary to provide skirts in a choice of internal shapes and sizes to suit the chosen cup shape and size. The loading tube can also be provided in a similar choice of diameters, but an expandable tube could be set to the required diameter and fixed with a circumferential strap, an inserter, for example, in the form of a piston of appropriate dimensions being employed.

Figure 11:
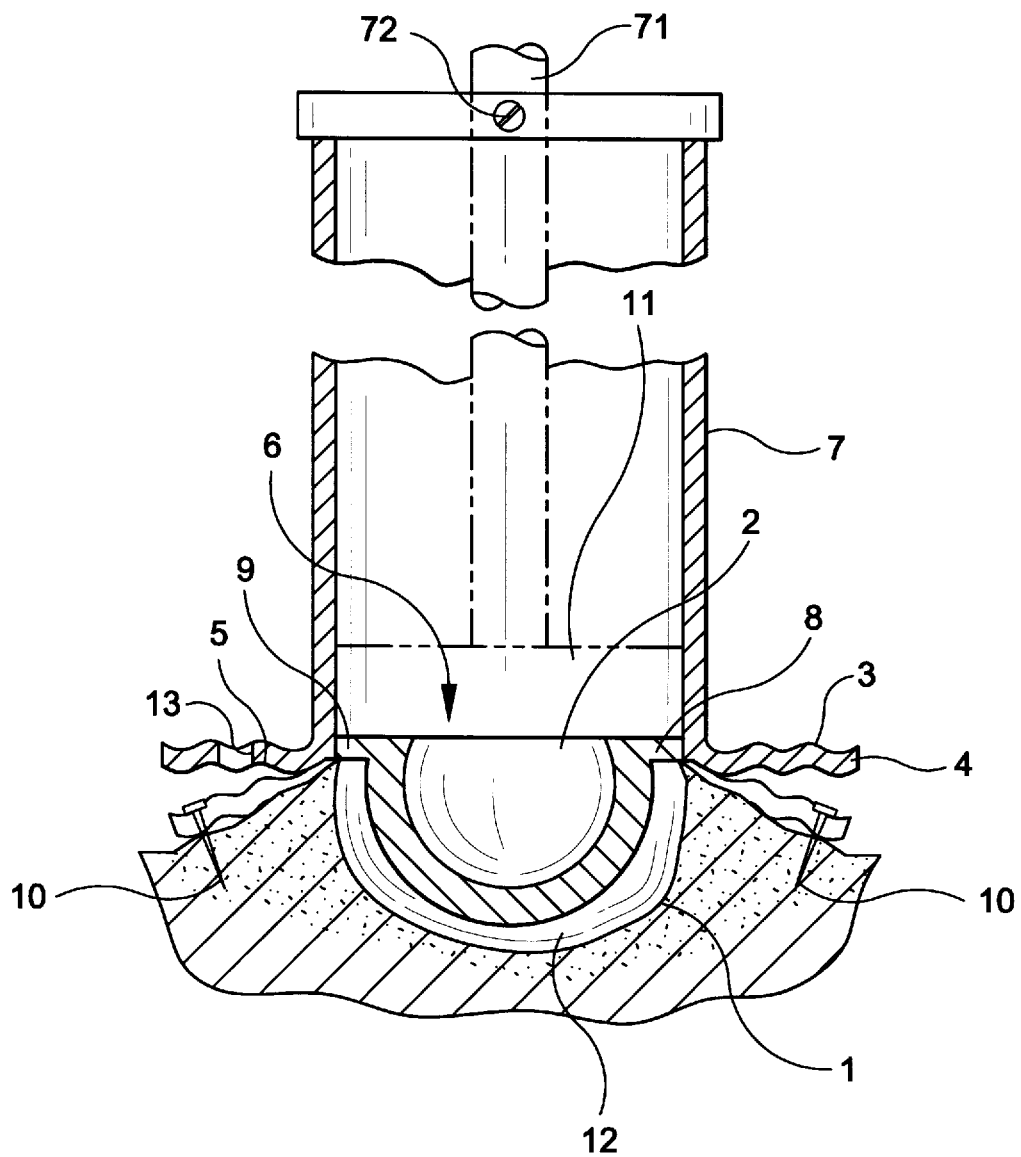

FIG. 11 shows another method and construction in which the cup can be accurately located in the socket and the same reference numerals are used to indicate similar parts to those shown in FIG. 1. With this construction, however, stop means are provided in the form of an adjustable disc 70 carried on a piston rod 71 of the piston 11. The disc 70 is held by a grub screw 72 passing through the disc and bearing against the piston rod 71. The screw 72 can be released to allow adjustment of the disc 70 on the rod 71.

As will be seen from FIG. 11, a cup 2 with a full projecting annular flange 9 is used but the position of the cup in the socket 12 is located by adjustment of the disc 17 which acts to limit the movement of the piston 11. As with the construction shown in FIG. 1, the tube 7 and the flange 3 can be removed completely after the cement has cured or the tube can be cut away and the flange 3 left in place. If desired, an adjustable loading tube as shown in FIG. 2 can be used.

Figure 2:
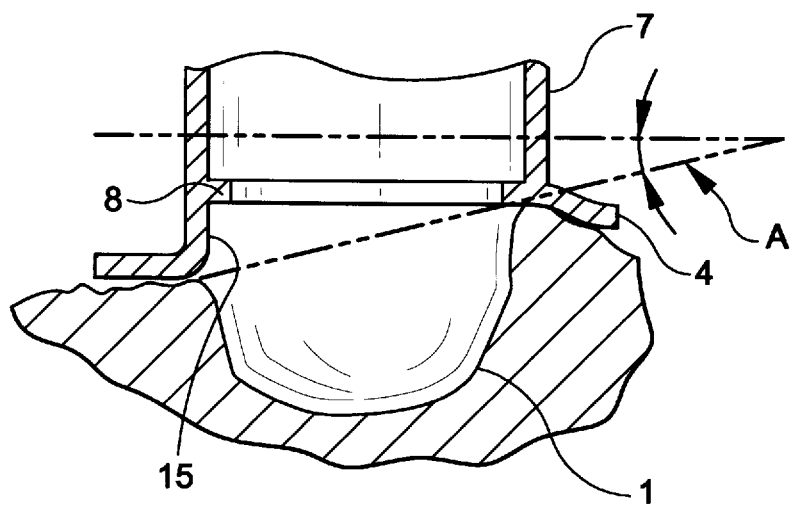
FIG. 2 is a diagrammatic side view of another form of the apparatus which would be supplied as a series of designs with a wedge or sloping orientation to accommodate deformed acetabular socket rims.

FIG. 2 shows a construction of combined skirt 4 and tube 7 which can be used for deformed/eroded acetabular rims. The tubes and skirts can be supplied as a series of designs with a wedge or slope orientation to accommodate different angles of deformity, the slope angle in FIG. 2 is indicated by reference numeral "A".

As can be seen in FIG. 2, in this construction the length of the lower end of the inner bore wall 15 varies about the diameter to provide the angled effect shown. A piston 11 and stop element are used as shown in FIG. 11, but if desired the stop element of FIG. 1 could be utilized, a suitable abutment being provided on the inner bore wall.

The series of designs could, of course, also be provided in different sizes as well as in wedge/ramp angles. This construction can also be provided by arranging for the skirt 4 and lower part of the tube wall 15 to be deformable so that the desired shape and wedge/ramp angle is formed by the operating surgeon. The natural bony rim of the acetabulum is not a uniplanar circular feature and if desired, the surgeon can machine a step around the rim to receive a sealing feature or the like.

Figure 3:
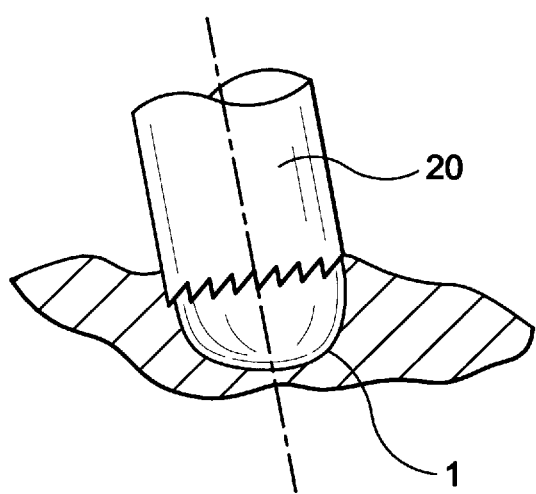
FIGS. 3, 4 and 5 show how a step can be machined around the rim of the acetabulum showing how the apparatus can be used if the bony rim is eroded.
Figure 4:
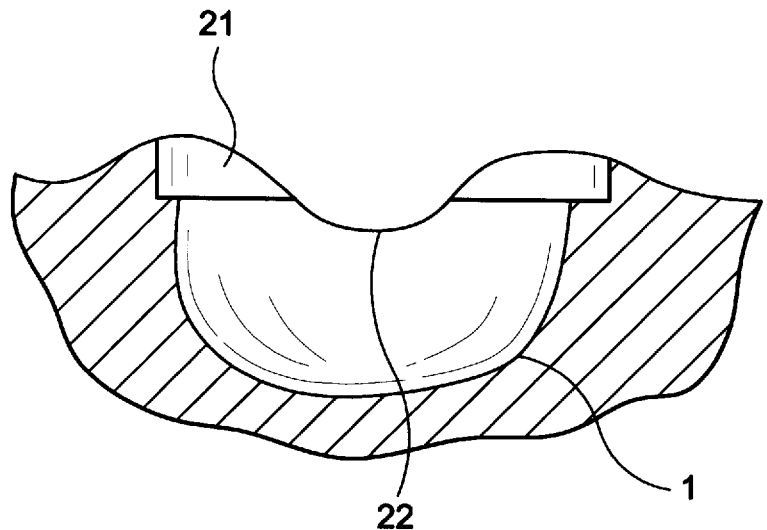
Figure 5:
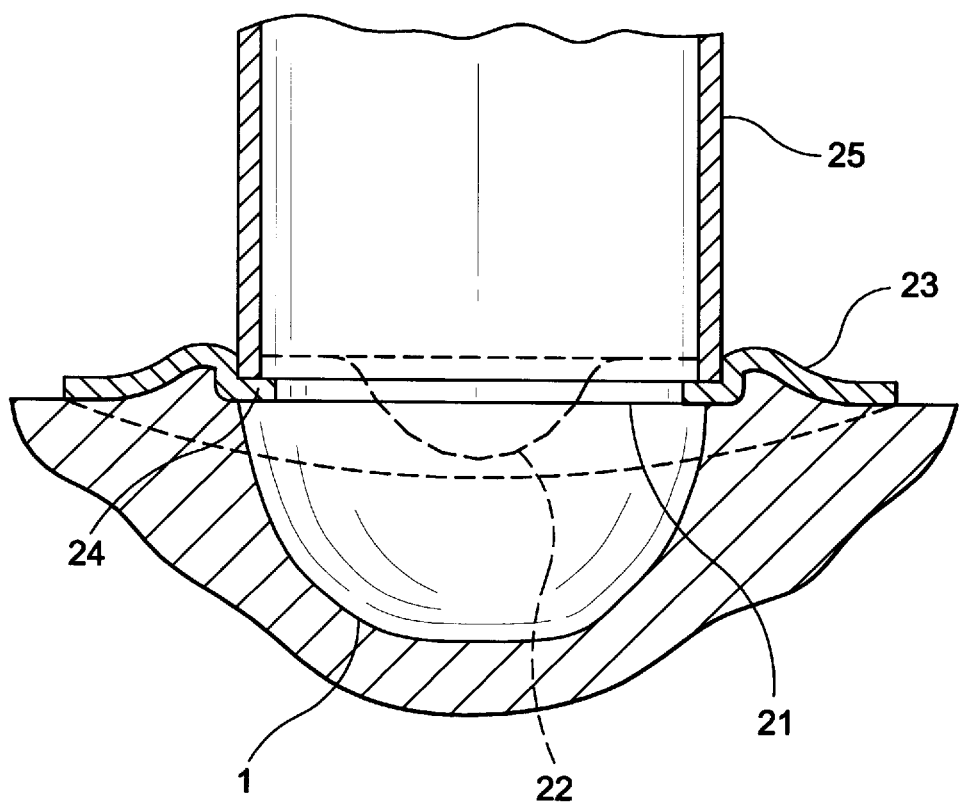

FIGS. 3 and 4 show how a trepanning cutter 20 is used to machine the rim depth to provide a step 21 inside the natural bony rim. The natural depression in the rim of the acetabulum is indicated by reference numeral 22. FIG. 5 shows how a skirt 23 can be used which provides an inwardly directed ledge 24 when placed on the step 21. The skirt extends upwardly and then outwardly and a removable loading tube 25 is placed in position on it. As will be seen from FIG. 5, the deformable skirt 23 is large enough to extend around and cover the natural dip 22 and prevent loss of cement when the piston 11 is operated. Once again, the stop element can be as shown in FIG. 1 or FIG. 11, and an adjustable tube can be used if desired.

The tube 25 can be arranged so that it is a relative push fit into the walls of the step 21 where they are covered by the upstanding portion of the skirt 23. It will be appreciated that a fixed tube 25 fixed to the skirts 4 could be used if desired.

In present surgical techniques, positioning and orientating an acetabular cup is sometimes achieved using a cup introducer/inserter with two alignment pointers, one of which points at 90° across the center line (axis of symmetry) of the patient and the other points vertically. This controls only orientation. Position and depth of insertion are chosen by the surgeon by eye.

Figure 6:
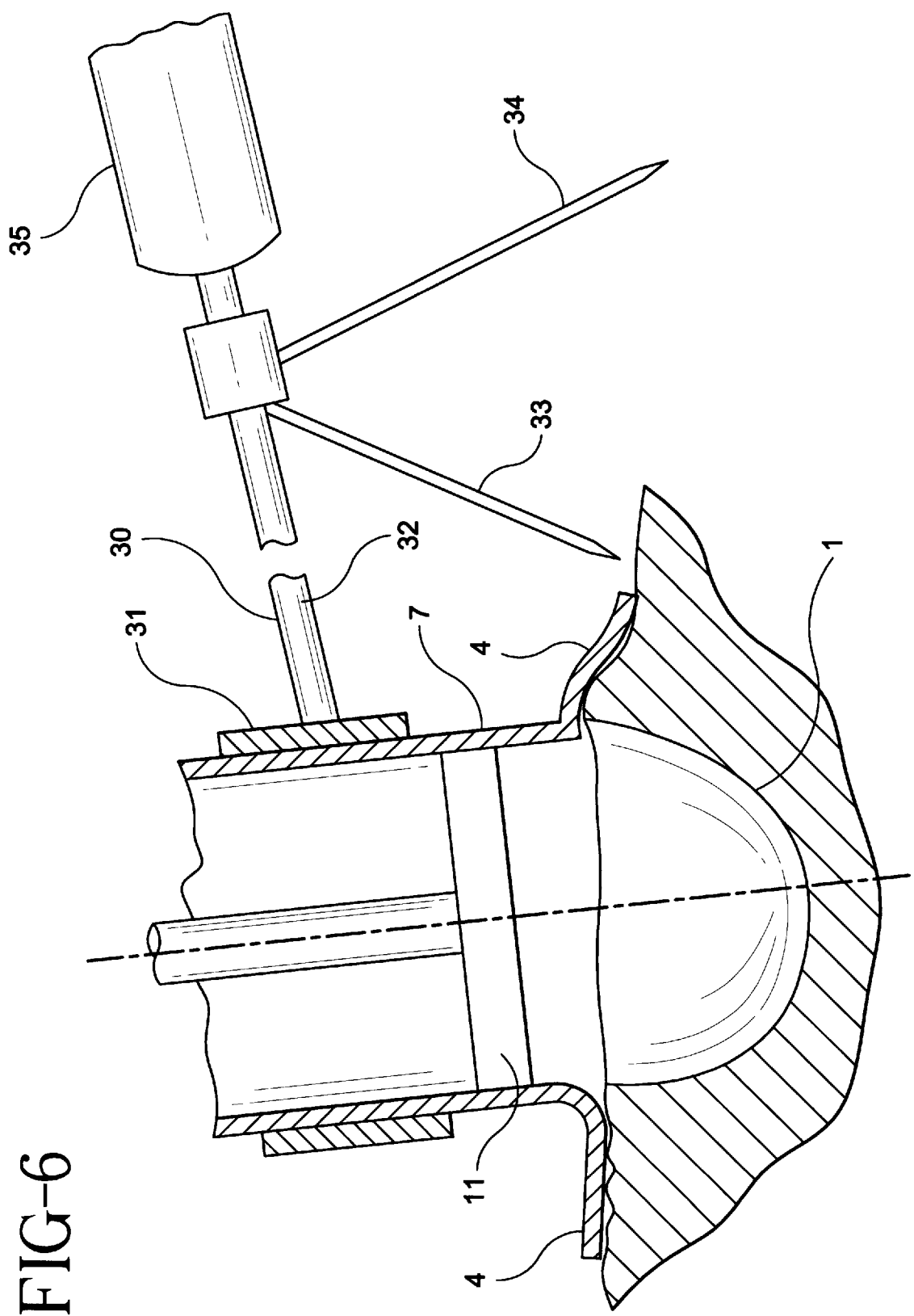
FIG. 6 shows in diagram form how an orientation guide can be provided.

In the construction shown in FIG. 6, the same reference numerals are used to indicate parts as shown in FIGS. 1 and 2 and an orientation guide 30 is provided which has a carrier 31 which surrounds the tube 7 and a long handle 32. The handle 32 carries adjustable alignment pointers 33, 34. The flexible skirt 4 can be steered by the handheld alignment and orientation guide 30 which is provided with a handle grip 35. The skirt is flexible enough to cope with deformed bony rims around the natural acetabulum and the alignment and orientation guide keeps everything in position and maintains the skirt 4 tight against the bone.

FIGS. 6, 7, 8 and 9 show an alternate method of employing the apparatus. An important task in this type of operation is to define the desired position and orientation of the cup. This is usually done by putting a trial or dummy implant in place. Theoretically, it could be determined before the operation using X-rays.

When using the present invention, it is necessary to place the tube and skirt such that the cup will eventually be positioned and tilted as required. The tube and skirt might be placed over a trial/dummy cup fixed and then the trial/dummy removed. Alternatively, the surgeon might remove the trial/dummy first and immediately fit the tube and skirt on the basis that his eyeball judgment of position and orientation is good enough.

Figure 7:
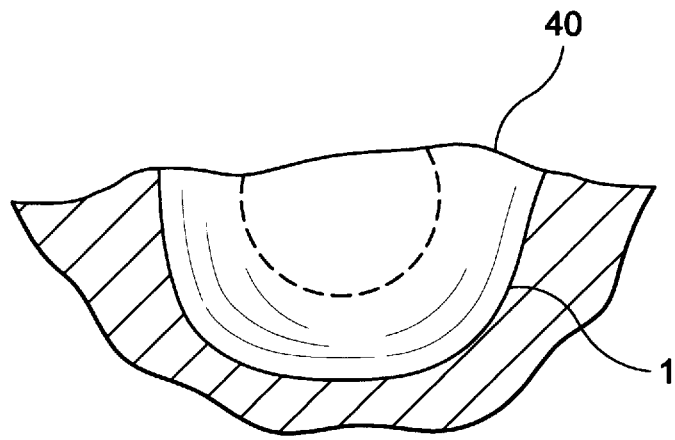
FIGS. 7, 8 and 9 show three steps in performing the method and using the apparatus when using a trial cup.

FIG. 7 shows a prepared acetabulum 1 into which a trial acetabular cup 40 has been fitted. At this stage the surgeon chooses the position of center and orientation.

Figure 8:
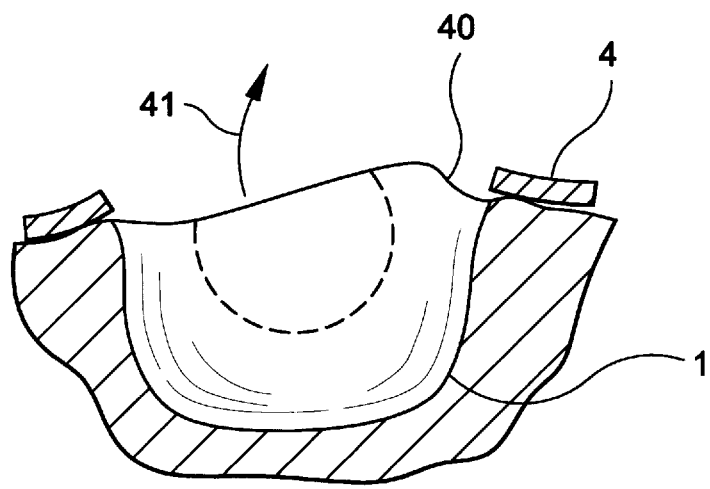

FIG. 8 shows how the surgeon can now fit the flexible skirt 4 around the trial cup 40 and the trial cup can then be removed, as indicated by arrow 41, without disturbing the skirt 4. After the trial cup 40 has been removed, leaving the flange in place, there is space for the loading tube (with or without an internally projecting abutment 8 according to the apparatus used) to be assembled to the skirt 4, for example as shown in FIG. 9, and for the implant equivalent to the trial cup 40 but necessarily smaller in size to be put in position.

Figure 9:
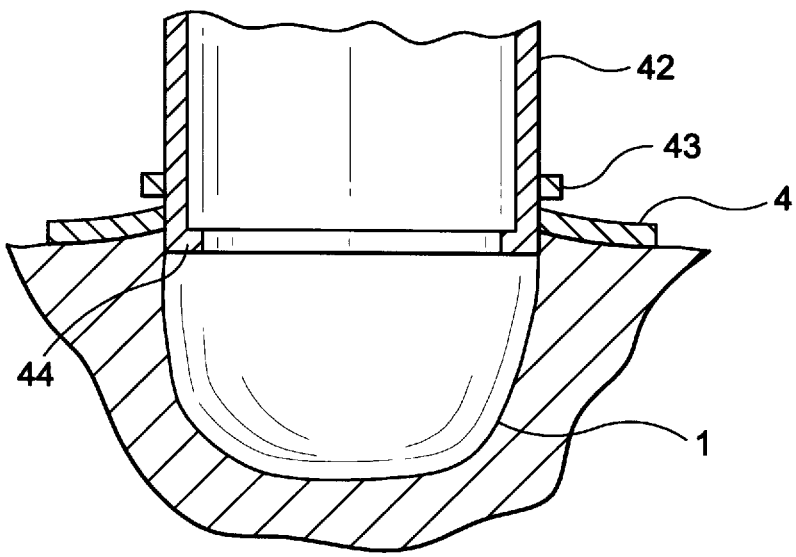

FIG. 9 shows one way of carrying out the procedure referred to above by using a separable loading tube 42 which is pushed into place within the opening in the skirt 4, the flexible construction of the skirt enabling the tube to be pushed into place with a tight, sliding fit. If desired, a depth stop abutment ring 43 can be provided to control the insertion of the tube into the skirt, as shown in FIG. 9. Due to the deformities of the natural acetabulum, this abutment ring 43 will not necessarily contact the skirt around the full periphery. If desired, the abutment ring 43 could be a tight sliding fit on the tube 42 so that it could be moved under pressure on the tube to provide a further adjustable depth stop.

Figure 10:
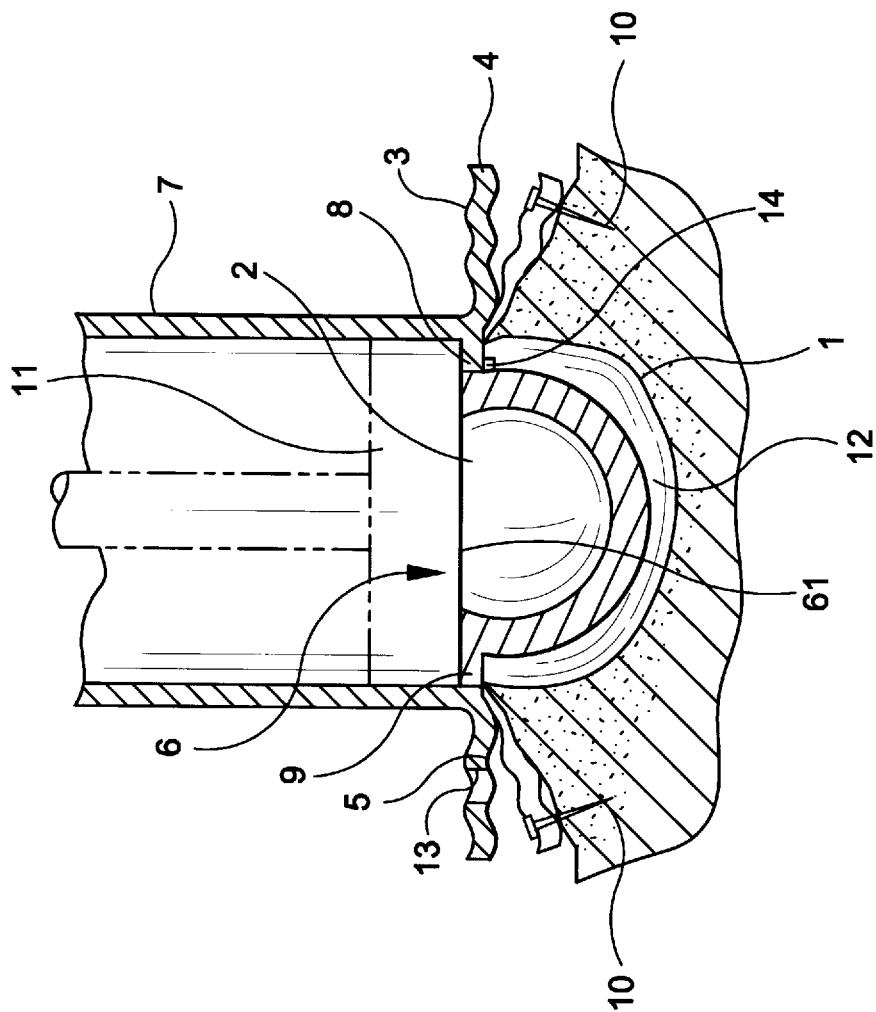
FIGS. 10 and 11 are views of alternate embodiments of the present invention.

FIG. 10 shows the piston 11 at its lower most position allowed by abutment 8. A portion of the gap 14 in flange 9 which allows the cup flange to pass through abutment 8 is also shown.

The lower end of the tube can have an abutment to provide stop means, or an arrangement as shown in FIG. 1 car be used. The tube can be cut away once the cup has been inserted or can be simply dismantled from the cup and skirt.

Figure 12:
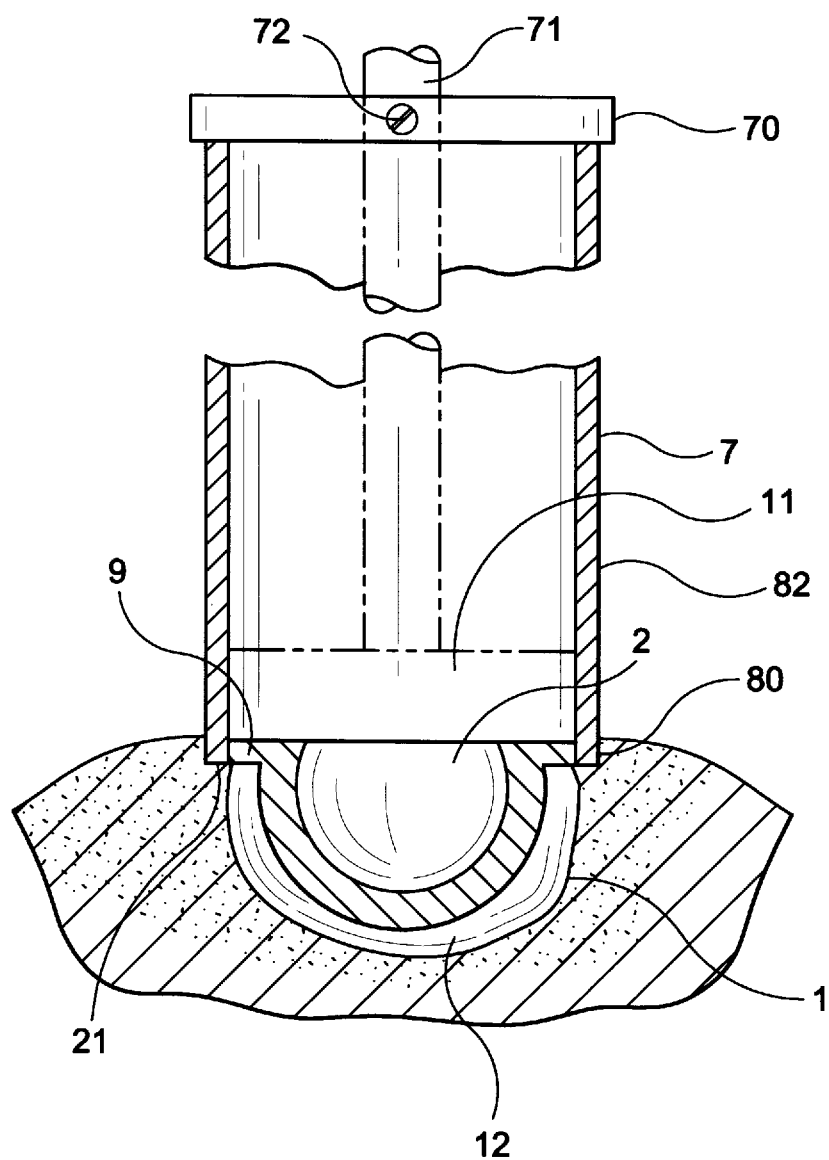

In FIG. 12 another method of implanting the cup 2 is shown and the same reference numerals as those used in FIG. 11 are again used to indicate similar parts. With this method no skirt 4 is used. The surgeon first prepares the socket 12 in the usual way and then employs a trepanning cutter in the manner shown in FIG. 3 and 4 to provide a step 21 inside the natural bony rim. The outer wall 80 of the step 21 is dimensioned so that the outer wall 81 of the tube 7 is a push fit onto the step 21.

In order to implant the cup the surgeon first places the tube 7 in position on the step 21 and the cement is then pushed into place by manual operation of the piston 11. The piston is removed when the cement is partially set and in an adequately doughy stage. The cup is now immediately inserted down the tube 7 and the cement is pressurized from the moment the cup touches it. The cup is pushed further downwards into the socket 12 to the desired position provided by the adjustable disc 17.

A tube and piston construction as shown in FIG. 1 can alternatively be used in a similar manner. An adjustable tube 7 can be used, for example, of the kind shown in FIG. 1. Once again, it will be seen from the drawing that no spacers are required in the cement mantle 12.

The essence of the present invention is to provide continuous cement pressurization during the fitting of the socket and accurate location of the cup in the acetabular socket.

It will be appreciated that variations of the various embodiments described can be made by incorporating the different details and the method may vary by incorporating the different methods described together.

We claim:

1. A method of implanting an acetabular cup prosthesis in an acetabular socket comprising the steps of:

preparing an acetabular socket to receive an acetabular cup, said cup having an outer diameter at a trailing end thereof;

placing cement in said socket;

locating a tube in line with said socket said tube having an inner diameter;

inserting an acetabular cup through the tube and into said socket with said trailing end facing outward; and pressurizing the bone cement with a means for sealing said inner diameter of said tube, said means located adjacent said trailing end of said cup.

2. The method of implanting an acetabular cup as claimed in claim 1 further including the step of locating a flexible skirt assembly around a rim of said socket, said tube extending from said flexible skirt, and inserting the acetabular cup through the tube and into the socket.

3. The method of implanting an acetabular cup as claimed in claim 2 further including the step of securing the flexible skirt around the rim of the socket to prevent the escape of cement and allowing the cement to be pressurized.

4. The method of implanting an acetabular cup as claimed in claim 3 further including the step of removing the tube and leaving the flexible skirt secured to the rim after the cup has been located.

5. The method of implanting an acetabular cup as claimed in claim 3 which includes removing the skirt after location of the cup and setting of the cement.

6. The method of implanting an acetabular cup as claimed in claim 3 which includes the step of holding the flexible skirt in place by attachment elements.

7. The method of implanting an acetabular cup as claimed in claim 2 further including the step of pressuring the cement and controlling the pressure of the pressurized cement by allowing the cement the escape from the socket and through a controlled orifice in the skirt.

8. The method of implanting an acetabular cup as claimed in claim 2 in which the tube is integral with the flexible skirt.

9. The method of implanting an acetabular cup as claimed in claim 2 in which the flexible skirt is removably connected to the tube.

10. The method of implanting an acetabular cup as claimed in claim 2 in which said flexible skirt is made from a synthetic plastics material.

11. The method of implanting an acetabular cup as claimed in claim 10 in which said flexible skirt is made from polyethylene, polypropylene, or polyurethane.

12. The method of implanting an acetabular cup as claimed in claim 2 in which said flexible skirt is made from a resorbable material.

13. The method of implanting an acetabular cup as claimed in claim 12 in which said flexible skirt is made from polyglycolic acid or polylactic acid.

14. The method of implanting an acetabular cup as claimed in claim 2 which includes the steps of placing the cup inside the tube and locating the cup within the tube in relation to a locating element formed on the tube.

15. The method of implanting an acetabular cup as claimed in claim 14 in which said locating element in said locating step is a projecting collar formed on the inside of the tube, which collar is dimensioned to engage a flange on said cup with which it is to be used.

16. The method of implanting an acetabular cup as claimed in claim 15 which includes the step of using an inserter in the form of a piston insertable within said tube to push cement down the tube.

17. The method of implanting an acetabular cup as claimed in claim 16 which includes using said inserter for pushing said cement to push the cup down the tube.

18. A method of implanting an acetabular cup prosthesis in an acetabular socket comprising the steps of:

preparing an acetabular socket to receive an acetabular cup;

placing cement in said socket;

locating a tube in line with said socket;

locating a flexible skirt assembly around the rim of said socket, said tube extending from said flexible skirt;

inserting the acetabular cup having a gap in a flange thereon through the tube and into said socket; and placing the cup inside the tube and locating the cup within the tube orienting said gap in said flange in relation to a locating element in the form of an abutment on the inner diameter of the tube.

19. The method of implanting an acetabular cup as claimed in claim 18 in which said locating element is a projecting collar formed on the inside of the tube, which collar is dimensioned to engage a flange on a cup with which it is to be used.

20. The method of implanting an acetabular cup as claimed in claim 19 which includes the step of using an inserter in the form of a piston to push cement down the tube.

* * * * *

UNITED STATES PATENT AND TRADEMARK OFFICE
CERTIFICATE OF CORRECTION

PATENT NO. : 5,879,402
DATED : March 9, 1999
INVENTOR(S) : Lawes et al.

Page 1 of 1

It is certified that error appears in the above-identified patent and that said Letters Patent is hereby corrected as shown below:

Column 1,
Line 40, "spacer" should read -- spacers --.

Column 2,
Line 32, "From" should read -- from --.

Column 3,
Line 34, "s" should read -- is --.
Line 58, "b" should read -- by --.
Line 64, "it is" should read -- in its --.

Column 4,
Line 13, after "place", insert -- with --.

Column 5,
Line 9, "is" should read -- are --.
Line 62, "is" should read -- are --.

Column 6,
Line 28, "car" should read -- can --.

Column 7,
Line 30, "the" (second occurrence) should read -- to --.

Signed and Sealed this

Twenty-fifth Day of September, 2001

*Attest:*

*Attesting Officer*

NICHOLAS P. GODICI
*Acting Director of the United States Patent and Trademark Office*